US007759496B2

(12) United States Patent
Järvinen et al.

(10) Patent No.: US 7,759,496 B2
(45) Date of Patent: Jul. 20, 2010

(54) IMIDAZOLE DERIVATIVES HAVING AFFINITY FOR ALPHA 2 RECEPTORS ACTIVITY

(75) Inventors: Tomi Järvinen, Kuopio (FI); Riku Niemi, Kajaani (FI); Juhani Huuskonen, Jyväskylä (FI)

(73) Assignee: Orion Corporation, Espoo (FI)

( * ) Notice: Subject to any disclaimer, the term of this patent is extended or adjusted under 35 U.S.C. 154(b) by 492 days.

(21) Appl. No.: 10/537,622

(22) PCT Filed: Dec. 5, 2003

(86) PCT No.: PCT/FI03/00933

§ 371 (c)(1),
(2), (4) Date: Mar. 29, 2006

(87) PCT Pub. No.: WO2004/050635

PCT Pub. Date: Jun. 17, 2004

(65) Prior Publication Data

US 2006/0178417 A1 Aug. 10, 2006

(30) Foreign Application Priority Data

Dec. 5, 2002 (FI) ................................. 20022159

(51) Int. Cl.
*A61K 31/4164* (2006.01)
*C07D 233/64* (2006.01)

(52) U.S. Cl. .................................... 548/335.1; 514/396

(58) Field of Classification Search ............... 548/335.1
See application file for complete search history.

(56) References Cited

U.S. PATENT DOCUMENTS

| | | | | |
|---|---|---|---|---|
| 4,673,679 | A * | 6/1987 | Aungst et al. | 514/282 |
| 5,658,938 | A | 8/1997 | Geerts et al. | |
| 6,313,311 | B1 | 11/2001 | Karjalainen et al. | |
| 6,388,090 | B2 | 5/2002 | Huhtala et al. | |
| 2005/0014828 | A1* | 1/2005 | Murthy et al. | 514/554 |
| 2007/0185181 | A1* | 8/2007 | Heino et al. | 514/396 |

FOREIGN PATENT DOCUMENTS

| | | | |
|---|---|---|---|
| EP | 0 717 037 | A1 | 6/1996 |
| JP | 10/195056 | A * | 7/1998 |
| WO | WO 97/12874 | | 4/1997 |
| WO | WO 00/18400 | | 4/2000 |
| WO | WO 01/30347 | A1 | 5/2001 |
| WO | WO 01/51472 | A1 | 7/2001 |
| WO | WO 03/099795 | | 12/2003 |

OTHER PUBLICATIONS

Thompson et al., Current Medicinal Chemistry, Oct. 2002, 9(19), pp. 1751-1762.*
Brown, Neurology, Jun. 25, 2002, 58(12), pp. 1720-1725.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Bundgaard, Drugs of the Future, 1991, 16(5), pp. 443-458.*
Bundgaard, A Textbook of Drug Design and Development, Harwood Academic Publishers, 1991, Chapter 5, pp. 113-191.*
R. Makabe, "Ophthafmologische Untersuchungen mit Dichlorphenylamlnoimidazolin," Dtsch. med. Wschr., 91, Jg., Nr. 38, 23, pp. 1686-1688 (1966).
Esler, M. et al. "Increase sympathetic nervous system activity and its therapeutic reduction in arterial hypertension, portal hypertension and heart failure," *J. Autonomic Nervous System* (1998) 72:210-219.
Lal, H. et al. "Psychopharmacology of Clonidine: An Introduction," *Psychopharmacology of Clonidine* (1981) Alan R. Liss, Inc., New York, NY: 1-3.
Gold, M. S. et al. "Neuroanatomical Sites of Action of Clonidine in Opiate Withdrawal: The Locus Coeruleus Connection," *Psychopharmacology of Clonidine* (1981) Alan R. Liss. Inc., New York, NY: 285-298.
Gold, M. S. et al. "Clinical Utility of Clonidine in Opiate Withdrawal: A Study of 100 Patients," *Psychopharmacology of Clonidine* (1981) Alan R. Liss, Inc., New York, NY: 299-306.

* cited by examiner

*Primary Examiner*—Laura L. Stockton
(74) *Attorney, Agent, or Firm*—Finnegan, Henderson, Farabow, Garrett & Dunner, LLP

(57) ABSTRACT

Novel prodrugs of MPV-2426, methods for preparing said prodrug forms, pharmaceutical compositions containing such prodrug forms, and methods for using the prodrug forms. A compound of general formula (I), (I)

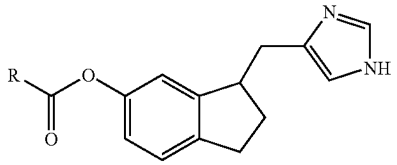

or pharmaceutically acceptable salts or hydrates thereof, wherein R represents unsubstituted or substituted lower alkyl, unsubstituted or substituted aryl, unsubstituted or substituted cycloalkyl, unsubstituted or substituted heteroaryl, unsubstituted or substituted lower alkylamino or a saturated five or six membered heterocyclic group containing one or two nitrogen atoms.

6 Claims, 1 Drawing Sheet

IMIDAZOLE DERIVATIVES HAVING AFFINITY FOR ALPHA 2 RECEPTORS ACTIVITY

This application is a U.S. national stage filing of PCT international application no. PCT/FI03/000933, filed on Dec. 5, 2003, which claims the benefit of priority to Finnish patent application no. 20022159, filed on Dec. 5, 2002.

FIELD OF THE INVENTION

The present invention relates to novel bioreversible prodrugs of MPV-2426, which is an $alpha_2$ adrenergic agonist, and specifically to ester derivatives, to methods for preparing said prodrug forms, to pharmaceutical compositions containing such prodrug forms, and to methods for using the prodrug forms.

BACKGROUND OF THE INVENTION

MPV-2426 [4-(6-hydroxyindan-1-ylmethyl)-1H-imidazol-1-ium chloride] is disclosed in U.S. Pat. No. 6,313,311 B1 as an $alpha_2$ agonist useful in the treatment of hypertension, glaucoma, migraine, diarrhea, ischemia, addiction to chemical substances, anxiety, e.g. preoperative anxiety, and different neurological, musculoskeletal, psychiatric and cognition disorders as well as a sedative and an analgesic agent, nasal decongestant, and as an adjunct to anaesthesia. MPV-2426 provides a spatially restricted and effective antinociception with minor side effects. Intraspinal, intrathecal or epidural administration of MPV-2426 is disclosed in WO 00/18400 A1. The treatment of hypotension, shock, and cardiopulmonary resuscitation by administering MPV-2426 is disclosed in WO 01/30347 A1.

$Alpha_2$ agonists are known to decrease intraocular pressure (IOP). The first report of the IOP lowering effects of these therapeutic agents was published in 1966 [Makabe, R. *Dtsch. Med. Wochenschr.,* 91 (1966) 1686].

Prodrugs are pharmacologically inactive derivatives of drug molecules that after chemical or enzymatic transformation release the active drug exerting the therapeutic action. Prodrugs are designed to overcome various pharmaceutical or biopharmaceutical problems associated with the parent drug. A prodrug with good permeation across biological membranes should exhibit optimum lipophilicity. In addition, a prodrug should be stable enough against chemical degradation and revert to the active parent drug via enzymatic hydrolysis in the body during or after absorption.

SUMMARY OF THE INVENTION

The present invention provides novel bioreversible ester prodrugs of MPV-2426 that are chemically stable in non-enzyme medium, have suitable lipophilicity (able to permeate through biological membranes) and readily hydrolyze to the parent drug in vivo.

The invention may also provide compounds for the manufacture of a medicament to be used in the treatment of hypertension, glaucoma, migraine, diarrhea, ischemia, addiction to chemical substances, hypotension, shock, cardiopulmonary resuscitation, micturition disorders, withdrawal syndromes, congestive heart failure, anxiety, e.g. preoperative anxiety, or different neurological, musculoskeletal, psychiatric or cognition disorders or as a sedative or an analgesic agent, nasal decongestant or as an adjunct to anaesthesia. In addition, the invention provides pharmaceutical compositions comprising as an active agent a compound of the invention. Furthermore, the invention provides methods for the treatment of diseases or conditions, wherein $alpha_2$ agonists are indicated to be useful, said method comprising to a mammal in need of such treatment an effective amount of a compound of the invention.

Additional embodiments of the invention will be set forth in part in the description, which follows, and in part will be obvious from the description, or may be learned by practice of the invention. The embodiments of the invention will be realized and attained by means of the elements and combinations particularly pointed out in the appended claims.

It is to be understood that the foregoing general description and the following detailed description are exemplary and explanatory only and are not restrictive of the invention as claimed.

DETAILED DESCRIPTION OF THE INVENTION

Figure 1:
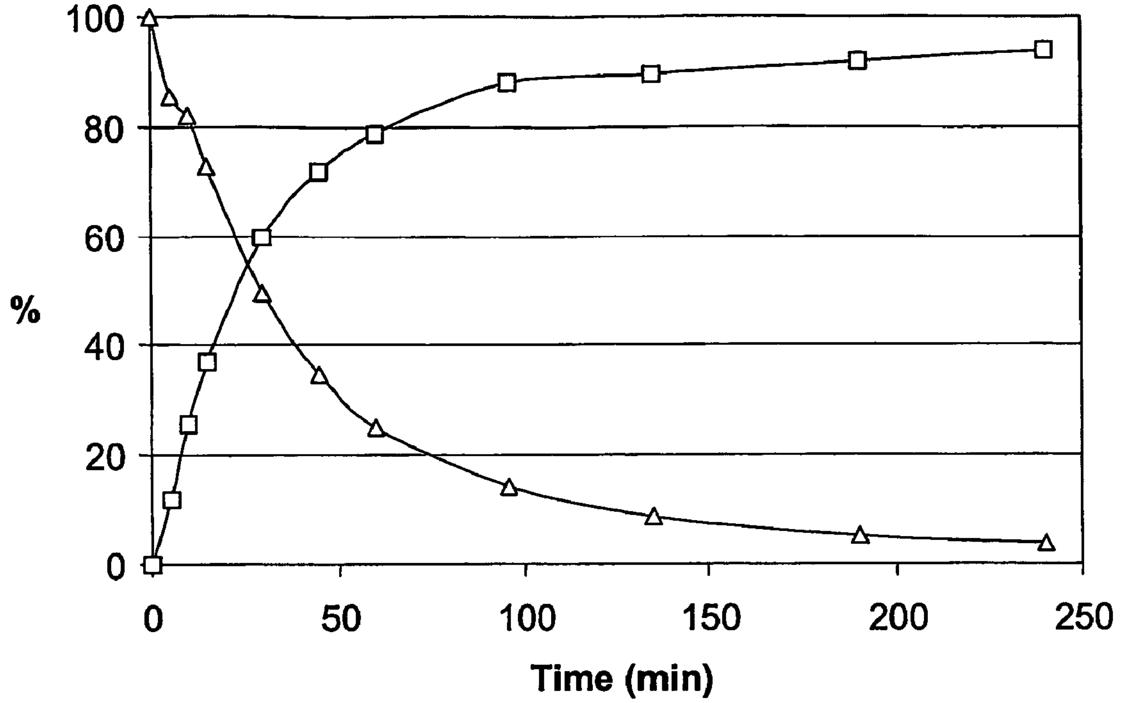
FIG. 1 shows the formation of MPV-2426 (□) upon hydrolysis of its pivaloyl ester (Δ) in 80% human serum at 37° C.

The present invention provides novel bioreversible ester prodrugs of general formula I, (I)

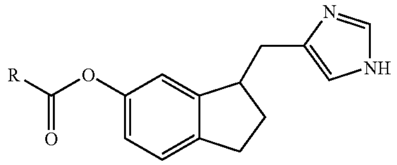

or pharmaceutically acceptable salts or hydrates thereof, wherein R represents unsubstituted or substituted lower alkyl, unsubstituted or substituted aryl, unsubstituted or substituted cycloalkyl, unsubstituted or substituted heteroaryl, unsubstituted or substituted lower alkylamino or a saturated five or six membered heterocyclic group containing one or two nitrogen atoms. For example, R represents unsubstituted or substituted lower alkyl or unsubstituted or substituted aryl, e.g. unsubstituted or substituted lower alkyl. Possibly, the compound is 4-[6-(2,2-dimethylpropanoyloxy)indan-1-ylmethyl]-1H-imidazol-1-ium chloride, 4-(6-acetoxyindan-1-ylmethyl)-1H-imidazol-1-ium chloride or 4-(6-butyryloxyindan-1-ylmethyl)-1H-imidazol-1-ium chloride. In the definitions of R, the term "lower" denotes residues with a maximum of 10 carbon atoms, e.g. a maximum of 6 carbon atoms. The term "alkyl" taken alone or in combination with terms such as "cycloalkyl" or "alkylamino" denotes straight or branched chain hydrocarbon residues. The term "aryl" denotes a carbocyclic aromatic group, possibly a mono- or bicyclic group. The term "heteroaryl" denotes a mono- or bicyclic aromatic group containing 1 to 3 heteroatoms being nitrogen and/or oxygen and/or sulfur, e.g. 1 or 2 heteroatoms being nitrogen and/or oxygen and/or sulfur. The term "substituted" in connection with various residues refers to hydroxy, cyano, nitro, halogen, amino, lower alkylamino, di(lower alkyl)amino, lower alkoxy, aryl or trifluoromethyl substituents. The substituted residues may contain 1 to 3 of said substituents, e.g. 1 or 2 of said substituents. The term "halogen" denotes fluorine, chlorine, bromine or iodine, e.g. chlorine or bromine.

Compounds of formula I may provide adequate lipophilicity and stability against chemical hydrolysis and revert to the active parent drug via enzymatic hydrolysis.

The invention may provide compounds for the manufacture of a medicament to be used in the treatment of hypertension, glaucoma, migraine, diarrhea, ischemia, addiction to chemical substances, hypotension, shock, cardiopulmonary resuscitation, micturition disorders, withdrawal syndromes, congestive heart failure, anxiety, e.g. preoperative anxiety, or different neurological, musculoskeletal, psychiatric or cognition disorders or as a sedative or an analgesic agent, nasal decongestant or as an adjunct to anaesthesia. In addition, the invention provides pharmaceutical compositions comprising as an active agent a compound of the invention. Furthermore, the invention provides methods for the treatment of diseases or conditions, wherein $alpha_2$ agonists are indicated to be useful, said method comprising to a mammal in need of such treatment an effective amount of a compound of the invention.

The compounds of the invention can be prepared by a variety of synthetic routes analogously to or according to the methods known in the literature using suitable starting materials.

In general, compounds of formula I, or pharmaceutically acceptable salts or hydrates thereof, can be prepared e.g. analogously to or according to scheme 1, wherein R is as defined above.

Scheme 1

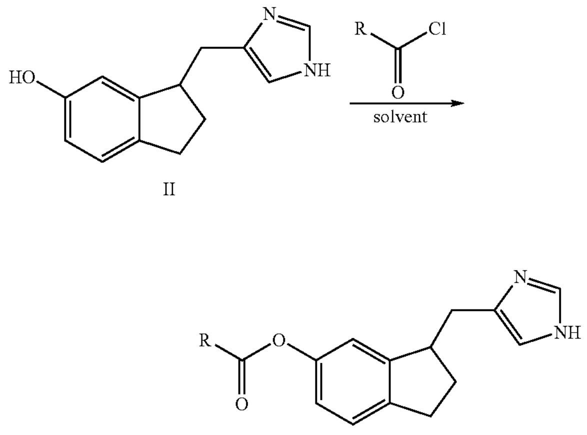

II

I

Hydroxyindan compound II, or a pharmaceutically acceptable salt or hydrate thereof, is dissolved in a solvent, e.g. trifluoroacetic acid (TFA), and a carboxylic acid chloride is added. The mixture is stirred, for example, at room temperature, for example, for 24 h. The solvent is evaporated and product compound I is isolated from the reaction mixture in a conventional manner. The compounds of the invention may be converted, if desired, into their pharmaceutically acceptable salts or hydrates using methods well known in the art.

The synthetic route described above is meant to illustrate the preparation of the compounds of the invention and the preparation is by no means limited thereto, i.e. there are also other possible synthetic methods which are within the general knowledge of a person skilled in the art.

EXAMPLE 1

4-(6-Acetoxyindan-1-ylmethyl)-1H-imidazol-1-ium chloride 4-(6-hydroxy-indan-1-ylmethyl)-1H-imidazol-1-ium chloride (100 mg, 0.399 mmol) was dissolved in 1 ml of trifluoroacetic acid (TFA) and acetic acid chloride (0.510 mmol) was added. The mixture was stirred at room temperature for 24 h. TFA was evaporated and the residue was dissolved in water and made basic with 2 M $NH_3$ (aq.). The aqueous phase was extracted with dichloromethane (DCM). The combined extracts were dried ($Na_2SO_4$) and evaporated. The residue was dissolved in diethyl ether and the solution was saturated with dry HCl gas. The precipitate was filtered and dried under vacuum. Yield 105 mg (82%) of a white hygroscopic solid. $^1$H NMR ($CDCl_3$, TMS): δ 1.72 (m, 1H), 2.18-2.26 (m, 4H), 2.72-2.87 (m, 3H), 3.17 (dd, 1H), 3.56 (qui, 1H), 6.85 (m, 2H), 6.92 (s, 1H), 7.16 (d, 1H), 8.61 (s, 1H), 14.44 (s, 2H). $^{13}$C NMR ($CDCl_3$, TMS): δ 21.11, 29.60, 30.46, 31.68, 43.93, 115.72, 117.00, 120.29, 125.33, 132.32, 132.40, 141.37, 146.32, 149.39, 170.11. HPLC-MS (EI): m/z=257.2 ($(M+H)^+$—$Cl^-$. Anal.—Calc. for $C_{15}H_{16}N_2O_2$.HCl.0.2$CH_2Cl_2$: C, 58.94; H, 5.66; N, 9.04. Found C, 58.66; H, 5.78; N, 8.83.

EXAMPLE 2

4-(6-Butyryloxyindan-1-ylmethyl)-1H-imidazol-1-ium chloride 4-(6-hydroxy-indan-1-ylmethyl)-1H-imidazol-1-ium chloride (100 mg, 0.399 mmol) and butyric acid chloride (510 mmol) were reacted in TFA (1 ml) and purified as described in example 1. Yield 90 mg (77%) of a white hygroscopic solid. $^1$H NMR ($CDCl_3$, TMS): δ 1.02 (t, 3H), 1.70-1.79 (m, 3H), 2.18-2.24 (m, 1H), 2.52 (t, 2H), 2.73-2.86 (m, 3H), 3.18 (dd, 1H), 3.53 (qui, 1H), 6.84 (dd, 1H), 6.87 (s, 1H), 6.92 (s, 1H), 8.66 (s, 1H), 11.28 (s (broad), 2H). $^{13}$C NMR ($CDCl_3$, TMS): δ 13.66, 18.45, 29.68, 30.52, 31.68, 36.24, 43.98, 115.79, 117.05, 120.36, 125.36, 132.32, 132.59, 141.32, 146.36, 149.51, 172.85.-HPLC-MS (EI): m/z=285.2 ($(M+H)^+$—$Cl^-$). Anal.—Calc. for $C_{17}H_{20}N_2O_2$.HCl.0.2$CH_2Cl_2$: C, 61.16; H, 6.39; N, 8.29. Found C, 61.30; H, 6.46; N, 8.22.

EXAMPLE 3

4-[6-(2,2-Dimethylpropanoyloxy)indan-1-ylmethyl]-1H-imidazol-1-ium chloride 4-(6-hydroxy-indan-1-ylmethyl)-1H-imidazol-1-ium chloride (100 mg, 0.399 mmol) and 2,2-dimethylpropionic acid chloride (510 mmol) were reacted in TFA (1 ml) and purified as described in example 1. Yield 74 mg (56%) of a white solid. M.p. 176-177° C. $^1$H NMR ($CDCl_3$, TMS): δ 1.33 (s, 9H), 1.69-1.78 (m, 1H), 2.16-2.25 (m, 1H), 2.74-2.88 (m, 3H), 3.23 (dd, 1H), 3.57 (qui, 1H), 6.83 (dd, 1H), 6.89 (s, 1H), 6.93 (s, 1H), 7.16 (d, 1H), 8.85 (s, 1H), 14.38 (s, 1H), 14.47 (s, 1H).

$^{13}$C NMR($CDCl_3$, TMS): δ 27.17, 29.64, 30.55, 31.57, 39.07, 43.95, 115.69, 116.96, 120.24, 125.33, 132.12, 132.66, 141.20, 146.30, 149.30, 177.87. HPLC-MS (EI):

m/z=297.7 ($M^+$-$2H^+$—$Cl^-$). Anal.—Calc. for $C_{18}H_{22}N_2O_2$.HCl: C, 64.57; H, 6.92; N, 8.37. Found C, 64.05; H, 7.00; N, 8.24.

EXPERIMENTS

A prodrug with good permeation across biological membranes should exhibit optimum lipophilicity (generally described as octanol-water partition coefficient, log $P_{app}$). In addition a prodrug should be stable enough against chemical degradation and revert to the active parent drug via enzymatic hydrolysis in the body during or after absorption.

EXPERIMENT 1

Lipophilicity

The lipophilicity was evaluated by determining apparent partition coefficients (log $P_{app}$) between 1-octanol and phosphate buffer pH 5.0 or 7.4 at room temperature. Generally log $P_{app}$ value in the range of 2-3 is considered optimal for absorption and membrane penetration in general.

Method

The apparent partition coefficients ($P_{app}$) were evaluated from the distribution of the test compounds between 1-octanol and phosphate buffer (0.16 M, pH 5.0 or pH 7.4, μ=0.5). The buffer and 1-octanol phases were saturated before use by stirring vigorously for 24 h at room temperature. A known concentration of the compound in phosphate buffer was shaken with a suitable volume of 1-octanol to achieve equilibrium. After 1 h shaking, the phases were separated by centrifugation and the concentration of the compound in the buffer phase was determined by HPLC.

Results

The log $P_{app}$ values of the compounds are given in Table 1. The lipophilicity of the compounds was substantially higher than that of the parent drug. Increased lipophilicity may result in enhanced membrane permeation as well as in longer duration of action as a consequence of altered pharmacokinetic properties (longer retention in the body).

TABLE 1

Apparent partition coefficients (log $P_{app}$, mean ± SD, n = 3) of MPV-2426 and its esters.

| Compound | log $P_{app}$ at pH 5.0 | log $P_{app}$ at pH 7.4 |
|---|---|---|
| MPV-2426 | 0.01 ± 0.02 | 1.87 ± 0.00 |
| example 1 | 0.13 ± 0.00 | 2.05 ± 0.01 |
| example 2 | 1.25 ± 0.01 | 3.17 ± 0.02 |
| example 3 | 1.75 ± 0.01 | 3.59 ± 0.03 |

EXPERIMENT 2

Chemical Stability

Method

An appropriate amount of the test compound (initial concentrations were 0.1-0.4 mM) was dissolved in pre-heated phosphate buffer (0.16 M, μ=0.5, pH 7.4 or pH 5.0). The solution was placed in a thermostated water bath at 37° C. and aliquots were taken at suitable intervals and analyzed by HPLC to determine the degradation rate of the compound. The pseudo-first-order half-life ($t_{1/2}$) was calculated from the linear slopes of semi-logarithmic plots of remaining compound over time.

Results

The degradation of the compounds in aqueous solution at pH 5.0 and 7.4 followed pseudo-first-order kinetics. The half-life ($t_{1/2}$) for the degradation is shown in Table 2. The stability of the compounds was substantially higher at pH 5.0 than at 7.4.

EXPERIMENT 3

Enzymatic Hydrolysis

To exert the pharmacological effect in the body, a prodrug should be enzymatically degraded to the parent drug. Therefore, the susceptibility of the compounds to serum esterases was evaluated.

Method

An appropriate amount of the test compound was dissolved in one volume (e.g. 1 ml) of phosphate buffer (0.16 M, μ=0.5, pH 7.4) at 37° C. Four volumes (e.g. 4 ml) of pre-heated human serum were added and the solutions were mixed in a water bath at 37° C. (initial concentrations were 0.2-0.5 mM). At suitable intervals, 300 μl aliquots were withdrawn and deproteinated with 600 μl of acetonitrile. After mixing and centrifugation, 600 μl of the supernatant was evaporated to dryness under a stream of air at 40° C. The residue was re-dissolved in 300 μl of the mobile phase and analyzed by HPLC. The pseudo-first-order half-life ($t_{1/2}$) was calculated from the linear slopes of semi-logarithmic plots of remaining compound over time. Also the formation of the parent drug was determined.

Results

The hydrolysis of the prodrugs in 80% human serum followed pseudo-first-order kinetics. The half-life ($t_{1/2}$) for the degradation is shown in Table 2. All the prodrugs

TABLE 2

Rate of hydrolysis in phosphate buffer solutions (pH 5.0 and 7.4) and in 80% human serum (pH 7.4) at 37° C.

| Compound | $t_{1/2}$ (d) phosphate buffer pH 5.0 | $t_{1/2}$ (d) phosphate buffer pH 7.4 | $t_{1/2}$ (min) 80% human serum (pH 7.4) |
|---|---|---|---|
| example 1 | 23 | 1.1 | 0.18 |
| example 2 | 49 | 2.5 | 0.20 |
| example 3 | 310 | 31 | 30 |

of MPV-2426 released the parent drug, MPV-2426, quantitatively via enzymatic hydrolysis in 80% human serum (pH 7.4). The formation of MPV-2426 upon hydrolysis of its pivaloyl ester in 80% human serum at 37° C. is illustrated in FIG. 1.

EXPERIMENT 4

IOP Study in Rabbits

The IOP study was performed to prove that the present prodrugs are able to release the parent drug and are thereby pharmacologically active in vivo. The IOP lowering effect of the prodrug was also compared to the effect of MPV-2426.

Method

To perform the IOP test, a rabbit was placed in a plastic restraining box located in a quiet room. A single drop (25 µl) of the test solution was instilled unilaterally into its left eye on the upper corneoscleral limbus. During installation, the upper eyelid was pulled slightly away from the globe. IOP was measured using a BioRad (Cambridge, Mass.) Digilab Modular One Pneumatonometer. Before each measurement one or two drops of oxybuprocaine (0.06%) were applied to the cornea before tonometry to eliminate discomfort. The upper and lower eyelids were then gently retracted, and the applanation sensor was brought into contact with the center of the cornea. For each determination at least two readings were taken from each treated (ipsilateral) and untreated (contralateral) eye, and the mean of these readings was used. IOP of the rabbits was measured at 2, 1, and 0 h before and at 0.5, 1, 2, 3, 4 and 5 h after eyedrop administration. IOP at the time of eyedrop administration (0 h) was used as a baseline value. All studies were set up using a masked and randomized crossover design. At least 72 h washout time was allowed for each rabbit between each dosing.

TABLE 3

Intraocular pressure (IOP) changes (mean mmHg ± SE, n = 5-6) at predetermined times (h) in the treated and untreated eyes of normotensive rabbits after unilateral administration of 25 µl of MPV-2426 or its pivaloyl ester (PIV) solutions in phosphate buffer pH 5.0.

| | TIME (h) | | | | | | |
|---|---|---|---|---|---|---|---|
| | 0 | 0.5 | 1 | 2 | 3 | 4 | 5 |
| Treated eye | | | | | | | |
| pH 5.0 buffer | 0.0 ± 0.0 | 1.5 ± 0.9 | −1.2 ± 1.2 | 0.1 ± 1.8 | −0.3 ± 1.3 | 0.0 ± 1.2 | 0.3 ± 2.0 |
| 0.1 µg of PIV | 0.0 ± 0.0 | 1.7 ± 0.9 | 0.2 ± 1.3 | 0.8 ± 1.2 | 0.6 ± 0.6 | 1.8 ± 0.5 | 2.0 ± 0.9 |
| 1.0 µg of PIV | 0.0 ± 0.0 | −1.0 ± 0.3 | −3.6 ± 0.7 | −4.6 ± 1.4 | −4.3 ± 1.1 | −2.0 ± 1.4 | −0.9 ± 1.8 |
| 2.5 µg of PIV | 0.0 ± 0.0 | 0.6 ± 0.9 | −2.9 ± 1.3 | −3.3 ± 1.8 | −1.6 ± 1.7 | 1.0 ± 2.2 | 1.3 ± 1.9 |
| 3.4 µg of PIV[a] | 0.0 ± 0.0 | −0.9 ± 0.9 | −2.9 ± 0.5 | −6.5 ± 1.1* | −5.2 ± 1.7 | −3.2 ± 0.9 | −1.4 ± 0.7 |
| 2.5 µg of MPV-2426 | 0.0 ± 0.0 | 0.1 ± 1.0 | −2.6 ± 1.1 | −3.0 ± 0.7 | −2.4 ± 0.5 | −0.4 ± 1.2 | −0.1 ± 0.8 |
| Untreated eye | | | | | | | |
| pH 5.0 buffer | 0.0 ± 0.0 | 0.2 ± 0.5 | −0.5 ± 0.4 | 0.8 ± 1.5 | −1.3 ± 0.7 | −0.7 ± 1.2 | −0.8 ± 1.3 |
| 0.1 µg of PIV | 0.0 ± 0.0 | 1.4 ± 0.1 | 0.9 ± 0.5 | 1.3 ± 0.2 | 1.3 ± 0.7 | 1.0 ± 0.9 | 2.4 ± 1.3 |
| 1.0 µg of PIV | 0.0 ± 0.0 | 0.0 ± 1.4 | −2.1 ± 1.2 | −2.0 ± 1.8 | −0.9 ± 2.4 | −1.4 ± 0.7 | −0.8 ± 2.1 |
| 2.5 µg of PIV | 0.0 ± 0.0 | −0.2 ± 0.9 | −0.6 ± 0.7 | 0.0 ± 1.5 | 0.1 ± 1.0 | 1.0 ± 1.8 | 0.3 ± 1.6 |
| 3.4 µg of PIV[a] | 0.0 ± 0.0 | 0.4 ± 0.7 | −2.7 ± 0.8 | −1.3 ± 0.6 | −2.8 ± 0.8 | −0.8 ± 0.7 | −0.8 ± 1.0 |
| 2.5 µg of MPV-2426 | 0.0 ± 0.0 | 0.3 ± 1.0 | −1.3 ± 0.7 | −1.6 ± 0.9 | −1.7 ± 0.6 | 0.4 ± 1.1 | 0.4 ± 1.1 |

[a]equimolar to 2.5 µg of MPV-2426

*data significantly different from values for MPV-2426, at a 95% confidence level (ANOVA, Fisher's PLSD test)

Results

The change in intraocular pressure (IOP) after topical unilateral administration of three different doses (0.1 µg, 1.0 µg, and 2.5 µg) of the pivaloyl ester of MPV-2426 is shown in Table 3. The IOP lowering effect lasted from 1 h through the duration of the 5 h experiment. Less significant changes were observed in the untreated eyes.

The pivaloyl ester of MPV-2426 showed increased IOP lowering potency as compared to an equimolar dose of MPV-2426 (Table 3). Also a prolonged duration of action was observed with the pivaloyl ester of MPV-2426.

The invention claimed is:

1. A prodrug 4-[6(2,2-dimethylpropanoyloxy)indan-1-ylmethyl]1H-imidazole or a pharmaceutically acceptable salt thereof.

2. The prodrug according to claim 1, wherein the compound is 4-[6-(2,2-dimethylpropanoyloxy)indan-1-ylmethy]-1H-imidazol-1-ium chloride.

3. A method for the treatment of hypertension, glaucoma, migraine, diarrhea, ischemia, addiction to a chemical substance, hypotension, shock, cardiopulmonary resuscitation, a withdrawal syndrome, congestive heart failure, anxiety, or for achieving sedation or analgesia, or for reducing nasal congestion, or for achieving anesthesia with an adjunct, which comprises administering to a mammal in need thereof an effective amount of a prodrug 4-[6-(2,2-dimethylpropanoyloxy)indan-1-ylmethyl]-1H-imidazole or a pharmaceutically acceptable salt thereof.

4. The method according to claim 3, wherein the prodrug is 4[6-(2,2-dimethylpropanoyloxy)indan-1-ylmethyl]-1H-imidazol-1-ium chloride.

5. A pharmaceutical composition which comprising a prodrug 4[6-(2,2-dimethylpropanoyloxy)indan-1-ylmethyl]-1H-imidazole or a pharmaceutically acceptable salt, and optionally a pharmaceutically acceptable excipient.

6. The pharmaceutical composition according to claim 5, wherein the prodrug is 4-[6-(2,2-dimethylpropanoyloxy)indan-1-ylmethyl]-1H-imidazol-1-ium chloride.

* * * * *